(12) United States Patent
Luginbühl et al.

(10) Patent No.: US 8,968,403 B2
(45) Date of Patent: Mar. 3, 2015

(54) IMPLANT DEVICE

(75) Inventors: Reto Luginbühl, Spiez (CH); Jürgen Vogt, Flüh (CH); Robert Mathys, Bettlach (CH); Beat Gasser, Ittigen (CH); Yannick Loosli, Biel (CH); Jorge Luis Sague Doimeadios, Bern (CH)

(73) Assignee: Dr. H.C. Robert Mathys Stiftung, Bettlach (CH)

( * ) Notice: Subject to any disclaimer, the term of this patent is extended or adjusted under 35 U.S.C. 154(b) by 419 days.

(21) Appl. No.: 13/001,854

(22) PCT Filed: Jul. 3, 2009

(86) PCT No.: PCT/EP2009/058431
§ 371 (c)(1),
(2), (4) Date: Mar. 16, 2011

(87) PCT Pub. No.: WO2010/000844
PCT Pub. Date: Jan. 7, 2010

(65) Prior Publication Data
US 2011/0166659 A1   Jul. 7, 2011

(30) Foreign Application Priority Data

Jul. 4, 2008 (EP) .................................. 08159741

(51) Int. Cl.
*A61F 2/08*   (2006.01)
*A61F 2/38*   (2006.01)
(Continued)

(52) U.S. Cl.
CPC ............. *A61F 2/389* (2013.01); *A61F 2/30965* (2013.01); *A61F 2/442* (2013.01); *A61F 2002/30014* (2013.01); *A61F 2002/30024* (2013.01); *A61F 2002/3895* (2013.01);
(Continued)

(58) Field of Classification Search
USPC ............................................. 623/17.11–17.16
See application file for complete search history.

(56) References Cited

U.S. PATENT DOCUMENTS 5,171,281 A * 12/1992 Parsons et al. ............. 623/17.15
5,534,028 A * 7/1996 Bao et al. ................... 623/17.16
(Continued)

FOREIGN PATENT DOCUMENTS

EP   0350127 A2   1/1990
EP   0642775 A1   3/1995
(Continued)

OTHER PUBLICATIONS

Biot, "Theory of Propagation of Elastic Waves in a Fluid-Saturated Porous Solid. II. Higher Frequency Range", The Journal of the Acoustical Society of America, Mar. 1956, pp. 179-191, vol. 28, No. 2.

*Primary Examiner* — Andrew Yang
*Assistant Examiner* — Olivia C Chang
(74) *Attorney, Agent, or Firm* — The Webb Law Firm

(57) ABSTRACT

The present invention is directed to an implant device, in particular an implant device placed between bony, cartilaginous or soft tissues or between prosthetic surfaces to restore or create a gap. More particular the present invention is directed to an implant device made from polymeric material and having a stiffness gradient as well as a limited dimensional deformation, wherein the implant device has a stiffness gradient and a limited dimensional deformation and preferably is at least partially anisotropic.

13 Claims, 7 Drawing Sheets

(51) Int. Cl.
  *A61F 2/30* (2006.01)
  *A61F 2/44* (2006.01)
(52) U.S. Cl.
  CPC . *A61F2250/0018* (2013.01); *A61F 2250/0021* (2013.01)
  USPC .................. 623/14.12; 623/17.16; 623/13.12

(56) References Cited

U.S. PATENT DOCUMENTS

| | | |
|---|---|---|
| 6,206,927 B1 | 3/2001 | Fell et al. |
| 6,558,421 B1 | 5/2003 | Fell et al. |

| | | | |
|---|---|---|---|
| 2004/0220672 A1 | 11/2004 | Shadduck | |
| 2005/0246021 A1* | 11/2005 | Ringeisen et al. | ......... 623/17.11 |
| 2005/0278025 A1 | 12/2005 | Ku et al. | |
| 2006/0241759 A1 | 10/2006 | Trieu | |

FOREIGN PATENT DOCUMENTS

| | | |
|---|---|---|
| EP | 0919209 A1 | 6/1999 |
| WO | 9319699 A2 | 10/1993 |
| WO | 2004108022 A1 | 12/2004 |
| WO | 2005077304 A1 | 8/2005 |
| WO | 2007139949 A2 | 12/2007 |
| WO | 2008064119 A2 | 5/2008 |

* cited by examiner

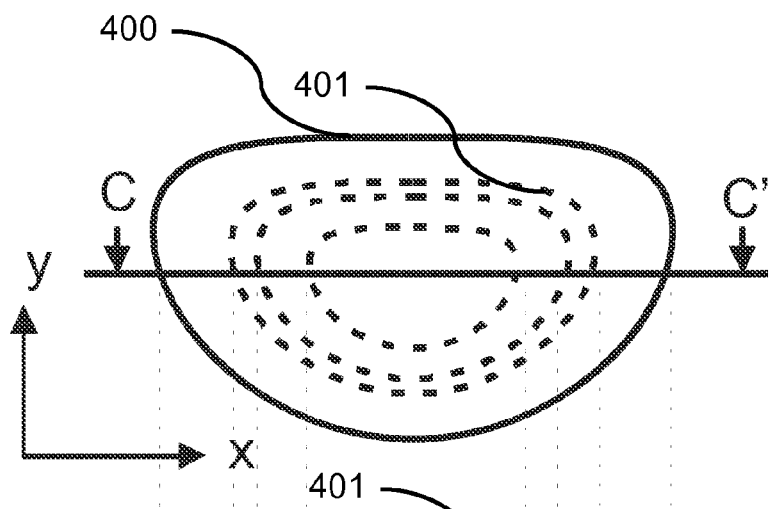
FIG. 10a
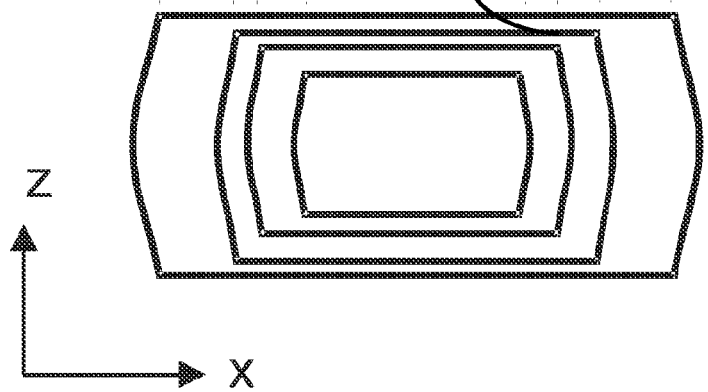
FIG. 10b
FIG. 10

IMPLANT DEVICE

The present invention is directed to an implant device, in particular an implant device placed between bony, cartilaginous or soft tissues or between prosthetic surfaces to restore or create a gap. More particular the present invention is directed to an implant device made from polymeric material, wherein the implant device has a stiffness gradient and a limited dimensional deformation and preferably is at least partially anisotropic.

BACKGROUND OF THE INVENTION

It is known, that joint hyaline cartilage degradation or damage due to trauma, intervertebral disc traumatic disease, or intervertebral chronic and progressive degeneration finally lead to local contact between bony surfaces. As these surfaces are in constant motion relative to each other, this contact leads to severe pain for the patient as well as to a further and accelerated destruction of the remaining compliant tissue.

Therefore restoring the gap between bones having an undesired contact will reduce pain, diminish or even anneal further destruction and may restore a balance closer to a healthy articulation. Several methods, aiming at the amelioration of the load bearing and/or articulation and at the prevention of further destruction of the compliant tissue, have been developed in the last decades.

Implants from cell culture allow the reparation of the tissue and reduce pain, but in general are very expensive, do not act as a gap filler and are not long lasting.

Articular cartilage and meniscal cartilage provide the mobile weight bearing surfaces of the knee joint. Damage to these surfaces is generally due to genetic predisposition, disease, trauma, and/or aging. The result is usually the development of chondromalacia, thinning and softening of the articular cartilage, and degenerative tearing of the cartilage. Most commonly, the cartilage is damaged by osteoarthritis. Articular cartilage has only limited ability to heal due to lack of a direct blood supply. Because the cartilage layer lacks nerve fibres, patients are often unaware of the severity of the damage. During the final stage of osteoarthritis, an affected joint consists of bone articulating against bone, which leads to severe pain and reduced mobility. By the time patients seek medical treatment, surgical intervention may be required to alleviate pain and repair the cartilage damage.

Various methods of treatment are available. Each option usually has specific indications and is accompanied by a list of benefits and deficiencies that may be compared to other options. Nonsteroidal anti-inflammatory drugs (NSAIDS), cortisone injections, hyaluronic acid injections, arthroscopic debridement, osteotomy, uni-compartmental knee replacement, and total knee replacement are used depending on the severity of the damage.

Currently, there is a void in options used to treat the relatively young patient with moderate to severe diseased or defective cartilaginous tissue involving mainly one compartment of the knee. Some patients cannot tolerate or do not want the risk of potential side effects of NSAIDS. Repeated cortisone injections actually weaken articular cartilage after a long period of time and do not protect the cartilage. Arthroscopic debridement alone frequently does not provide long lasting relief of symptoms. Uni-compartmental and bi-compartmental total knee replacements resect significant amounts of bone and may require revision surgery when mechanical failure occurs. Therefore, it is best to delay this type of bone resecting surgery as long as possible.

One approach has been to implant a compliant device in the inter-condylar void space. In theory, such devices cushion the femoral and tibial bearings surfaces and distribute loads uniformly over a larger portion of the knee joint due to the ability of these devices to elastically deform and ensure the gap between both bearing surfaces. This ability to deform can also be a detriment, with regard to the poor fatigue behaviour of such device undergoing too large deformation resulting into tearing or disintegration.

U.S. Pat. No. 6,206,927 discloses a self-centering meniscal prosthesis device suitable for minimally invasive, surgical implantation into the cavity between a femoral condyle and the corresponding tibial plateau. The prosthesis is composed of a hard, high modulus material shaped such that the contour of the device and the natural articulation of the knee exerts a restoring force on the free-floating device.

US-A-2005/278025 discloses a prosthesis for placement into a joint space between two or more bones. The prosthesis includes a body formed from a pre-formed solid one piece elastomer, wherein the elastomer is formed from a synthetic organic polymer that is biocompatible and has a uniform modulus of elasticity and a mechanical strength between 0.5 MPa and 75 MPa. Preferably, the body has a shape contoured to fit within a joint space between the femoral condyle, tubercle, and tibial plateau without any means of attachment. The prosthesis is uni-compartmental, i.e. is adapted for implantation into a compartment defined by the space between the tibial plateau and a femoral condyle. Thus, the prosthesis is suited for use in either a lateral compartment or a medial compartment. Where it is necessary to replace menisci in both compartments, two prostheses are required.

The intervertebral disc functions to stabilize the spine and to distribute forces between vertebral bodies. The intervertebral disc is composed primarily of three structures: the nucleus pulposus, the annulus fibrosis, and two vertebral end-plates. These components work together to absorb the shock, stress, and motion imparted to the human vertebrae. Intervertebral discs may be displaced or damaged due to trauma or disease. One way to relieve the symptoms of these conditions is by surgical removal of a portion or all of the intervertebral disc or by implanting an artificial device to replace the damaged portion of the patient's intervertebral disc.

WO-A-2004/108022 discloses an intervertebral disc implant that comprises an elastomeric polymer body, in particular a hydrogel body, and a super elastic element. The implant for the spinal disc space, in a preferred embodiment comprises an elongated hydrogel body and an elongated core element comprised of a super elastic nickel-titanium alloy.

US-A-2006/0241759 discloses a polymeric spinal implant wherein the polymer material is substantially uniformly oriented to create anisotropic properties, especially increased strength perpendicular to the orientation of the polymer material. In moulded polymeric materials, increased anisotropic rigidity or strength may be achieved by substantially orienting the polymer chains in the material during processing, for example by slowly cooling from melt state or by application of pressure (e.g. in an injection molding process).

WO-A-2007/139949 discloses a spinal intervertebral disc implant comprising a solid elastomeric body with mechanical compressive and/or tensile elasticity of from 1 MPa to 100 MPa. The implant can be configured with a single, uniform average durometer material and/or may have non-linear elasticity. The implant can be configured to be stiffer in the middle, or stiffer on the outside perimeter. The implant can further be configured to have a continuous stiffness change.

EP-A-0919209 discloses a prosthetic nucleus for a vertebral disc made of a hydrogel material and exhibiting diminished lateral bulging under high compressive loads, wherein the anterior periphery preferably has a stiffness of from 0.1 to 1.5 MPa, and the posterior periphery has a stiffness at least 10% less than that of the anterior periphery, wherein the increase in stiffness from the anterior to the posterior sides can be either gradual or sudden.

WO-A-2008/064119 discloses a multi-component implantable spinal disk comprising an external shell, a first endplate, a second endplate, plural attachment devices and a core internal component, wherein the external shell preferably has a Young modulus of elasticity of from 7 to 13 MPa and the core internal component has a Young modulus of elasticity of from 3 to 8 MPa, wherein the core internal component may comprise vertical reinforcement columns with a Young modulus of elasticity of from 6 to 13 MPa.

WO-A-2005/077304 generally discloses a multi-component load bearing biocompatible device, in particular an implantable spinal disc prosthesis, which may comprise multiple regions of varying elasticity. For example the upper portion and lower portion can be less elastic and more rigid than the inner region. The implantable spinal disc prosthesis further may have an intermediate region of elasticity.

EP-A-0642775 discloses a multi-component implantable spinal disc comprising a first and second endplate, wherein up to three layers of different polymers, preferably with different compressibility for each polymer, are arranged in between the two endplates to form the multi-component implantable spinal disc.

However, none of the prior art so far has been able to achieve a compliant material or device capable of providing structural and tribological properties similar to native tissue.

Surprisingly it has now been found that an implant device of the present invention solves the problems described above.

SUMMARY OF THE INVENTION

The present invention therefore, in one aspect, is directed to an implant device comprising a body having a stiffness gradient with at least one minimum along the x-axis and/or along the y-axis, wherein the body has a limited dimensional deformation capability in the direction of the x-axis and/or y-axis under maximum physiological load condition, characterized in that the dimensional deformation is below 10% in the direction corresponding to the x- and/or y-axis, based on the dimension under no load condition compared to the dimension under a maximum load condition. Preferably, the stiffness of the body is at least partially anisotropic.

In another aspect, the invention is directed to a method for manufacturing said implant device. In yet another aspect, the invention is directed to the use of said implant device for implantation into a human or animal body.

BRIEF DESCRIPTION OF THE DRAWINGS

FIG. 10a is a two-dimensional representation of an embodiment of an implant device according to the invention.

FIG. 10b is a two-dimensional sectional view of an implant device according to FIG. 10a along section C-C'.

DEFINITIONS

Figure 1:
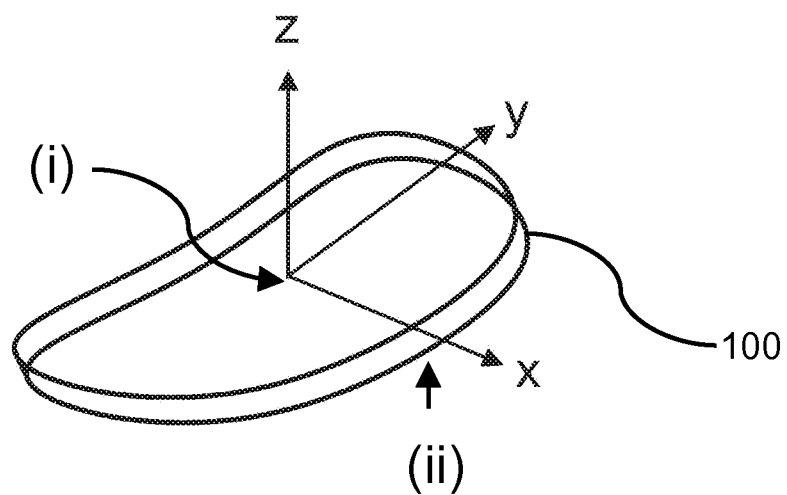
FIG. 1 is a three-dimensional schematic representation of one embodiment of an implant device according to the invention.

An << implant device >> according to the invention is a device to be implanted between bony, cartilaginous or soft tissues or between prosthetic surfaces to restore or create a gap. An << implant device >> preferably has two opposable surfaces at a defined distance, wherein the dimensions of the device in the direction parallel to the two opposable surfaces (i.e. width or diameter of the device) is larger than the dimension perpendicular to the opposable surfaces (i.e. thickness of the device). Examples for an << implant device >> are an inter-condylar or a spinal disc implant.

The << x-axis >> of an implant device is a first imaginary axis through the geometrical centre of the device in the direction substantially parallel to the two opposable surfaces, which is generally parallel to the medial-lateral axis. The << y-axis >> is a second imaginary axis through the geometrical centre of the device in the direction substantially parallel to the two opposable surfaces, but perpendicular to the << x-axis >>, which is typically parallel to the anterior-posterior axis. The << z-axis >> of an implant device is a third imaginary axis through the geometrical centre of the device in the direction perpendicular to the two opposable surfaces (i.e. perpendicular to the << x-axis >> and the << y-axis >>) often understood as being generally parallel to the caudal-cranial direction. Usually, the << z-axis >> is the direction of the main exerted force.

A << stiffness gradient >> in the context of the invention is a change of stiffness along either the x-axis or the y-axis or both, wherein the change may be continuous (i.e. according to a constantly differentiable function) or discontinuous (i.e. according to a step function or other not constantly differentiable functions). "Stiffness" in the context of the present invention is related to the device's material having an elastic contribution with a large modulus, i.e. a large aggregate modulus or hydraulic permeability as described in Biot M A, "Theory of propagation of elastic waves in a fluid saturated porous solid, I. Low frequency range", published in *The Journal of the Acoustical Society of America* 1956; 28:168-78. The aggregate modulus and/or the hydraulic permeability can be determined by a creep and/or relaxation compression test as generally know in the art. Another method known in the art to determine the "stiffness" is related to the device's material having a larger storage modulus, which is commonly used together with the loss modulus to characterize viscoelastic materials under dynamic load conditions.

It is to be understood that in the context of the invention "stiffness" is the opposite of "elasticity".

"Isotropy", by definition, is uniformity with regard to a particular property in all directions. An "at least partially isotropic" material is at least at close range symmetric (in its properties), whereas at far range said symmetry is not given. "Anisotropy" is the opposite of "isotropy". An "at least partially anisotropic" material is at least at close range not symmetric (in its properties), whereas at far range a symmetry may be given. An "orthotropic material" has two or three mutually orthogonal two-fold axes of rotational symmetry so that its mechanical properties (such as stiffness) are different along the directions of each of the axes. An orthotropic material is thus anisotropic.

A << limited dimensional deformation >> is a change in dimension, in particular in the x-y plane, which preferably is below 20%, more preferably below 10%, even more preferably below 5% and most preferably below 1%, based on the dimension under no load condition compared to the dimension under a maximum load condition, i.e. a relative dimensional deformation.

A << maximum physiological load condition >> for an implant device according to the invention corresponds to load conditions found in the physiological application area of the implant. Preferably the maximum load is 200 MPa, more preferably 100 MPa, most preferably 20 MPa.

<< Structural properties >> and << tribological properties >> in the context of the invention are generally referred to as << mechanical properties >> of a material or device. << Structural properties >> for example relate to the stiffness/elasticity, load distribution, stress/strain and fatigue behaviour of a material or device. << Tribological properties >> for example relate to the wear rate and the friction coefficient of a material or device.

An << interspace implant >> is a device for implantation into a spatial cavity between two articulating surfaces, in particular an inter-condylar implant or a << spinal disc implant >>, which is a device for implantation into a space defined by the disc nucleus or disc annulus.

The term << conforming to the physiological situation upon implantation >> in the context of the invention means that the shape of the device after implantation fills optimally the gap between the bearing surfaces.

The term << self-centering >> in the context of the invention means that the device has the ability to come back to the best suited location at the end of each cyclic body motion by the means of its geometry or its mechanical properties.

The term << biocompatible >>, as used herein, refers to the property of a material or the surface of a material, which may be in intimate contact with tissue, blood, or other body fluids of a patient for an extended period of time without significantly damaging the biological environment and without significantly causing patient discomfort.

DETAILED DESCRIPTION OF THE INVENTION

An implant device according to the present invention comprises a body having a stiffness gradient with at least one minimum along the x-axis and/or along the y-axis, wherein the body has a limited dimensional deformation in the direction of the x-axis and/or y-axis under maximum physiological load condition, characterized in that the relative dimensional deformation is below 10% in the direction corresponding to the x- and/or y-axis, based on the dimension under no load condition compared to the dimension under a maximum load condition.

In a preferred embodiment of the invention the stiffness of the body is at least partially anisotropic.

In one embodiment of the invention, the stiffness gradient is continuous. In another embodiment of the invention, the stiffness gradient is discontinuous.

In a preferred embodiment of the invention the body has a stiffness gradient with at least two minima along the x-axis and/or y-axis.

Preferably the stiffness properties of the implant device according to the invention are orthotropic.

In one embodiment of the invention, the implant device is an interspace implant, in particular an inter-condylar implant or a spinal disc implant. Preferably the interspace implant is an inter-condylar implant.

In another preferred embodiment of the invention, the shape of the implant device is conforming to the physiological situation upon implantation.

In still another preferred embodiment of the invention, the implant device is self-centering in the physiological space it is implanted in.

In yet another preferred embodiment of the invention, the implant device has a stiffness corresponding to a Young modulus ranging from at least 0.1 to 100 MPa in each direction when the material is modelled as linear elastic.

In yet another preferred embodiment of the invention, the implant device has a dynamic coefficient of friction below 0.1.

In a preferred embodiment of the invention, the body of the implant device is comprised of a polymer material. Preferably the body is entirely comprised of one type of polymer material. In another embodiment the body is comprised of several types of polymer materials.

More preferably the polymer material is a hydrogel.

Most preferably the polymer material is biocompatible.

In another aspect, the present invention is directed to a method for manufacturing an implant device as defined above, wherein the body is formed by a polymer material, wherein the stiffness gradient and/or the partial anisotropy is created (a) through partly orienting the molten or semi-molten polymer material, or (b) through a layer-by-layer curing and/or crosslinking process, or (c) through introducing oriented or non-oriented fibre reinforcement into part of the polymer material.

In a further aspect, the present invention is directed to the use of an implant device as defined above for implantation into a human or animal body.

DETAILED DESCRIPTION OF EMBODIMENTS

In FIG. 1, an interspace implant (100) according to the present invention is shown in a three-dimensional schematic representation. A Cartesian coordinate system (x-y-z-axis) is shown in relation to the body of the device, wherein the centre (i) and the edge (ii) are indicated.

Figure 2:
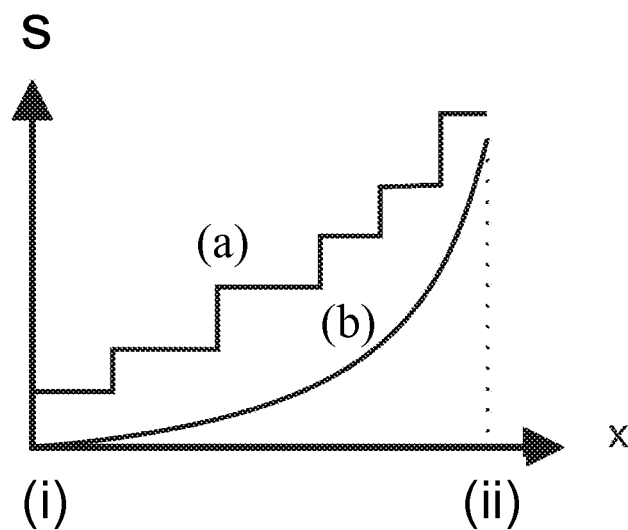
FIG. 2 is a graphic representation of the stiffness (S) of two different embodiments of implant devices according to the invention, depicting the possible change in stiffness (a) or (b) respectively, from the centre (i) to the edge (ii) of the device.

The stiffness (S) of two different embodiments of interspace implants according to FIG. 1 is depicted in FIG. 2. The change in stiffness along the x-axis from the centre (i) to the edge (ii) for the device (a) is discontinuous, whereas the change in stiffness along the x-axis from the centre (i) to the edge (ii) for the device (b) is continuous. Both devices would have a minimum stiffness at the centre (i).

Figures 3, 3A, 3B:
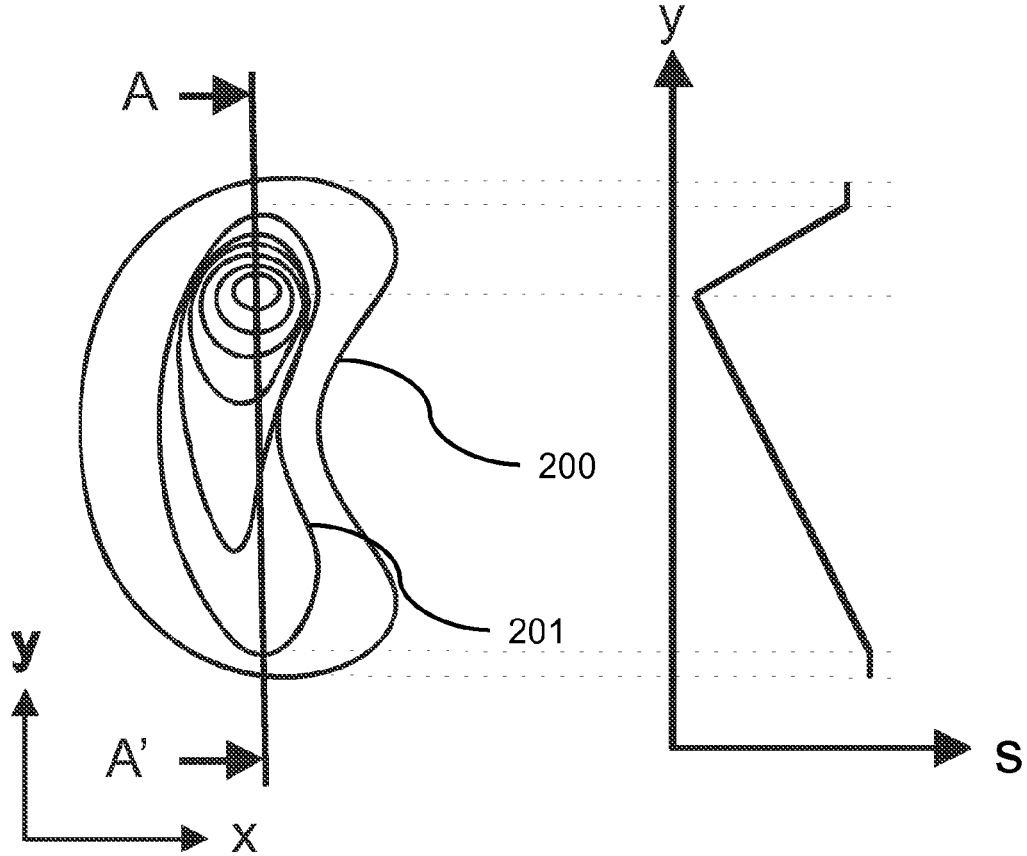
FIG. 3a is a two-dimensional representation of an embodiment of an implant device according to the invention.
FIG. 3b is a graphic representation of the stiffness (S) in direction of the y-axis at section A-A'.

FIG. 3 shows a uni-condylar knee implant (200), wherein the contour lines (201) are added only for illustration and are not to be understood as being discrete boundaries for changes in material properties. The interspace implant (200) in the embodiment as shown in FIG. 3a, has a stiffness that continuously changes at least along the y-Axis (section A-A'). The implant comprises material or material properties of higher stiffness (S) in the periphery and material or material properties of lower stiffness (S) in the central part. The stiffness continuously decreases from the periphery to the centre as depicted in FIG. 3b.

Figures 4, 4A, 4B:
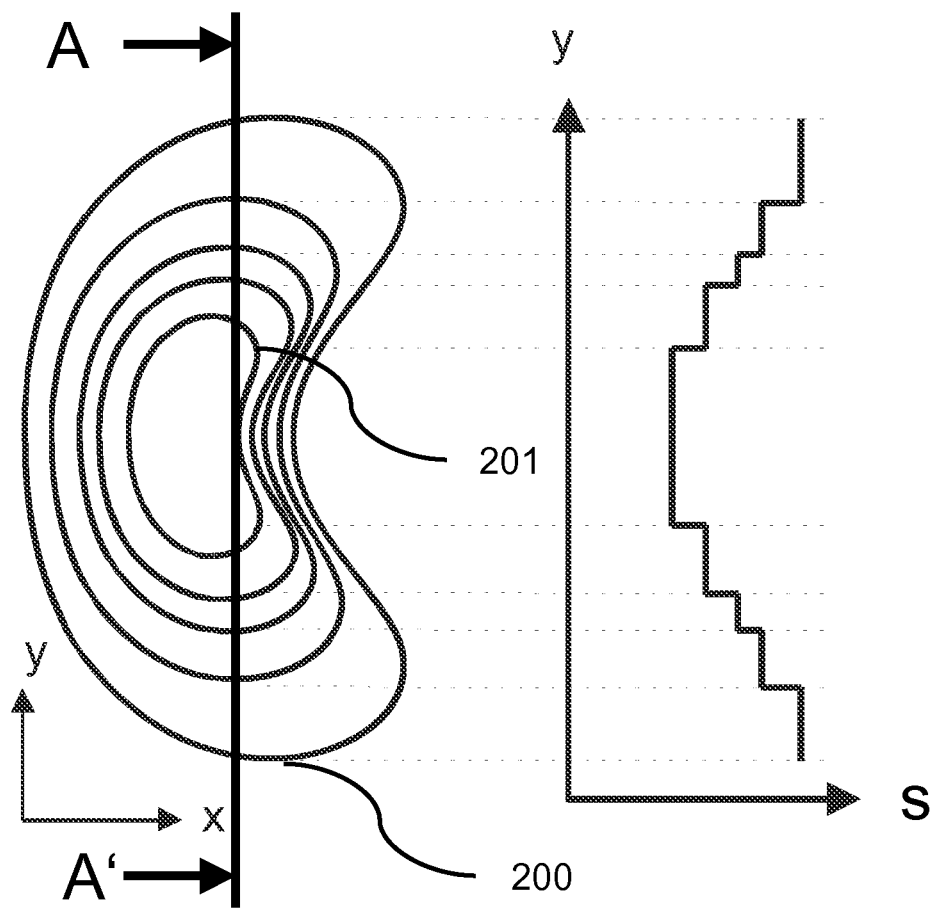
FIG. 4a is a two-dimensional representation of an embodiment of an implant device according to the invention.
FIG. 4b is a graphic representation of the stiffness (S) in direction of the y-axis at section A-A'.

FIG. 4 shows a uni-condylar knee implant (200), wherein the lines (201) are discrete boundaries for changes in material and/or in material properties. The interspace implant (200) in the embodiment as shown in FIG. 4a, has a stiffness that discontinuously changes at least along the y-Axis (section A-A'), i.e. changes according to a step function as depicted in FIG. 4b. The implant comprises material or material properties of higher stiffness (S) in the periphery and material or material properties of lower stiffness (S) in the central part. The stiffness of each concentric area closer to the central part is lower than the surrounding area. Thereby the stiffness is discontinuously decreasing from the periphery to the centre.

Figure 5:
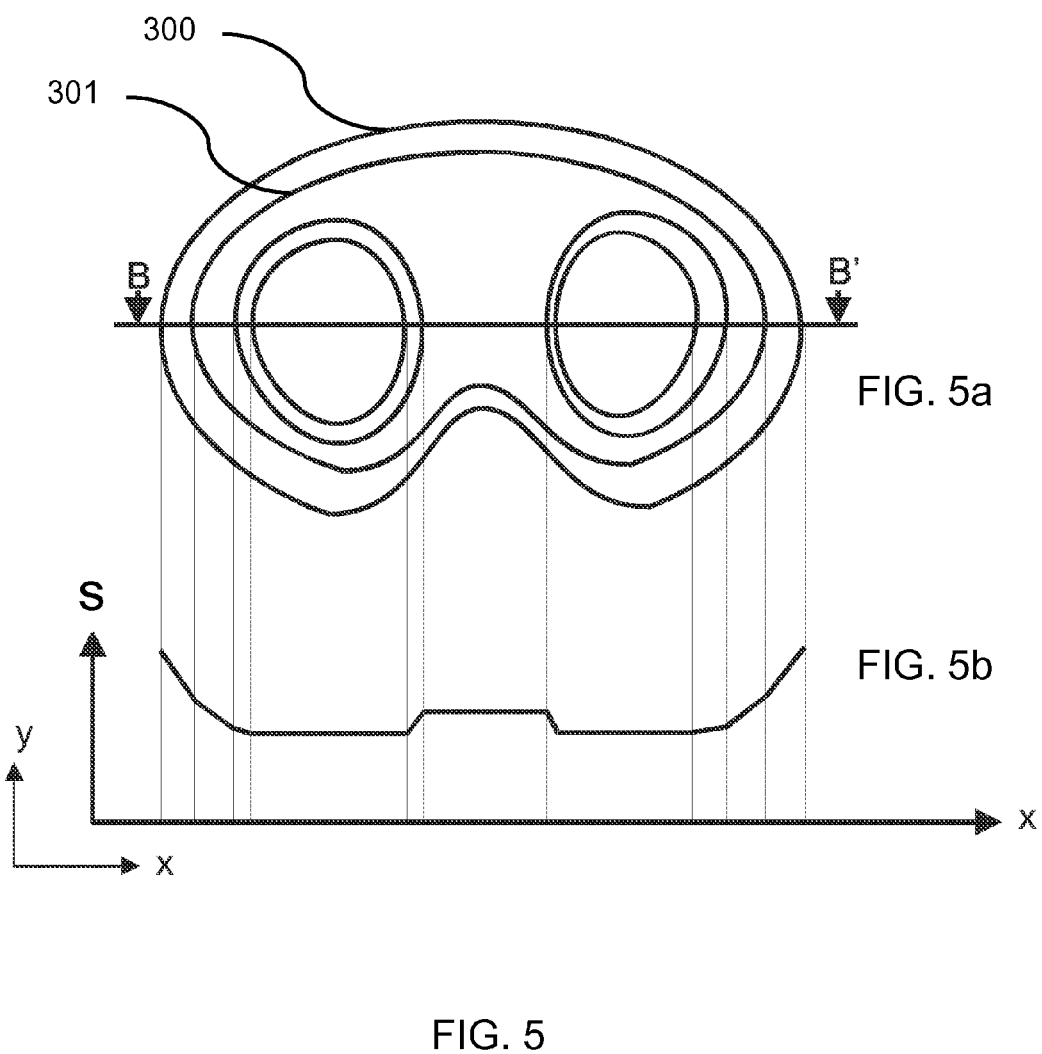
FIG. 5a is a two-dimensional representation of an embodiment of an implant device according to the invention.
FIG. 5b is a graphic representation of the stiffness (S) in direction of the x-axis at section B-B'.

FIG. 5 shows a bi-condylar knee implant (300), wherein the contour lines (301) are added only for illustration and are not to be understood as being discrete boundaries for changes in material properties. The interspace implant (300) in the embodiment as shown in FIG. 5a, has a stiffness that continuously changes along the x-Axis (section B-B') with a peripheral are, two areas of lower stiffness (S), and an intermediate area. The implant comprises material or material properties of higher stiffness (S) in the periphery and material or material properties of lower stiffness (S) in each of the two central areas. The stiffness of each concentric area closer to each of the two central parts is lower than the surrounding area. Thereby the stiffness is decreasing from the periphery to each of the two centres along the y-axis. Along the x-axis, however, there is an intermediate area between the two central parts where the stiffness increases, i.e. coming from one central part the stiffness increases before it again decreases towards the second central part. The stiffness along the x-Axis is depicted in FIG. 5b accordingly.

Figure 6A:
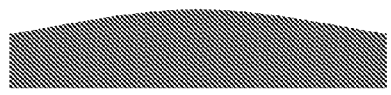
FIG. 6a is a schematic representation of a possible shape of an (uni-condylar) interspace implant according to the invention in sectional view, having one flat and one curved (convex) opposable surface.
Figure 6B:
FIG. 6b is a schematic representation of a possible shape of an (uni-condylar) interspace implant according to the invention in sectional view, having two curved (convex-convex) opposable surfaces.

FIG. 6a shows an uni-condylar knee implant according to the invention in sectional view, having one flat and one curved (convex) opposable surface. FIG. 6b shows another uni-condylar knee implant according to the invention in sectional view, having two curved (convex-convex) opposable surfaces.

Figure 7A:
FIG. 7a is a schematic representation of a possible shape of an (uni-condylar) interspace implant according to the invention in sectional view, having one flat and one curved (concave) opposable surface.
Figure 7B:
FIG. 7b is a schematic representation of a possible shape of an (uni-condylar) interspace implant according to the invention in sectional view, having two curved (concave-concave) opposable surfaces.

FIG. 7a shows an uni-condylar knee implant according to the invention in sectional view, having one flat and one curved (concave) opposable surface. FIG. 7b shows another uni-condylar knee implant according to the invention in sectional view, having two curved (concave-concave) opposable surfaces.

Figure 8:
FIG. 8 is a schematic representation of a possible shape of an (uni-condylar) interspace implant according to the invention in sectional view, having two curved (convex-concave) opposable surfaces.

FIG. 8 shows another uni-condylar knee implant according to the invention in sectional view, having two curved (convex-concave) opposable surfaces.

Figure 9:
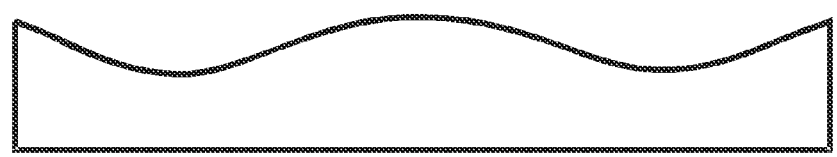
FIG. 9 is a schematic representation of a possible shape of a (bi-condylar) interspace implant according to the invention for example as shown in FIG. 5a (sectional view along section B-B').

FIG. 9 shows a bi-condylar knee implant according to FIG. 5a in sectional view along section B-B'.

FIG. 10 shows a spinal disc implant (400), wherein the lines (401) are discrete boundaries for changes in material and/or in material properties. As shown in FIG. 10a the spinal disc implant (400) is built from concentric areas, illustrated by the sectional view of FIG. 10b (along section C-C'), wherein each concentric area may have a different stiffness (S), which decreases from the periphery to the centre.

Figure 11:
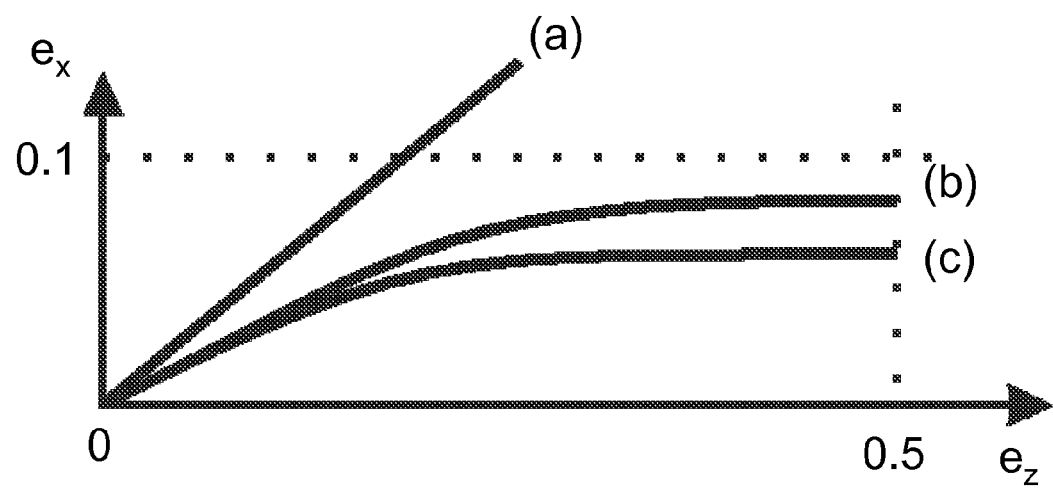
FIG. 11 is a graphic representation of the relation of the relative dimensional deformation under load condition along the x-axis ($e_x$) and the z-axis ($e_z$) for (a) a homogeneous material, (b) a bi-component material, and (c) a material with a continuous gradient.

FIG. 11 is a graphic representation of the relative dimensional deformation under load condition along the x-axis ($e_x$) and the z-axis ($e_z$) for (a) a homogeneous material, (b) a bi-component material, and (c) a material with a continuous (stiffness) gradient. The load is applied in the direction of the z-axis. The value of 0.5 for $e_z$ corresponds to a relative dimensional deformation of the respective implant device of 50% under load condition compared to the dimension in direction of the z-axis (i.e. the "thickness") under no load condition. Whereas the value of 0.1 for $e_x$ corresponds to a deformation of the respective implant device of 10% under load condition compared to the dimension in direction of the x-axis (i.e. the "width") under no load condition.

The homogeneous material (a) typically would be considered to be an isotropic material, whereas material (b) and (c) would be partially anisotropic.

Interspace implants according to the invention are suitable to be placed between almost any bony, cartilaginous or soft tissues or between prosthetic surfaces to restore or create a gap. For example in the condylar space between femur and tibia (i.e. a meniscal or knee implant), between vertebral bodies (i.e. a spinal disc implant) or between the tibia and the talus (i.e. an ankle implant), etc.

The material that forms the device of the present invention must be sufficiently strong to withstand repeated stresses caused by body motion e.g. during typical knee or spine movement. Preferably, the device has a stiffness corresponding to a Young modulus (E) ranging from 0.05 to 200 MPa, preferably from 0.1 to 100 MPa, and most preferably from 0.5 to 20 MPa, when the material is modelled as linear elastic.

In one embodiment of the invention, the implant device has a global Young modulus of at least 1 MPa enabling the device to withstand normal stress loading forces for 1 to 2 million cycles e.g. as typically experienced by human cartilage in a time period of 1 to 2 years.

The implant device of the invention has a dimensional deformation below 10% in the direction corresponding to the x- and/or y-axis, based on the dimension under no load condition compared to the dimension under a maximum load condition. The maximum load is to be understood as the physiological load resulting in a pressure in z-direction ranging from 20 MPa to 200 MPa depending on device application and patient. The deformation of the implant device under physiological load can be accompanied by a change in hydratization, in particular where the material of the implant device is a hydrogel material. Accordingly, a physiological load may lead to a change in hydratization and/or to a change in volume of the implant device. In particular each physiological load condition may correspond to a respective equilibrium hydratization and/or to a respective equilibrium volume of the implant device.

Furthermore, the material used to form the device of the present invention must have a sufficiently low coefficient of friction to enable the device to move for example within the inter-condylar compartment and withstand the repeated motion of the femoral condyle on the superior surface. Specifically, the coefficient of friction must be sufficiently low such that upon flexion and extension motions, the stress on the device created by the femoral condyle does not cause the device to unrecoverably unseat from the tibial plateau. Moreover a low friction should ensure only little wear during the walking gait. Preferably, the material has a dynamic coefficient of friction below 0.1, more preferably below 0.05, most preferably below 0.01. Preferably the material of the body of the implant device is a polymeric material, most preferably a hydrogel, comprising molecules of synthetic origin, natural origin, biotechnologically derived origin, or any combination thereof. Suitable polymeric materials are biocompatible.

Suitable synthetic polymeric materials include silicone, polyurethanes, copolymers of silicones and polyurethane, polyisobutylene, polyisoprene, neoprene, nitrile, vulcanized rubber, hydrogels formed from polyvinyl alcohol, polyacrylic acid, poly(acrylonitrile-acrylic acid), polyethylene glycol, poly(N-vinyl-2-pyrrolidone), poly(2-hydroxy ethyl methacrylate), copolymers of acrylates with N-vinyl pyrrolidone, N-vinyl lactams, acrylamide, polyacrylonitrile, thermoplastic polyurethanes, aliphatic polyurethanes, segmented polyurethanes, hydrophilic polyurethanes, polyether-urethane, polycarbonate-urethane, silicone polyetherurethane, crosslinked carboxyl-containing polysaccharides, polyesters, polyamides, polyethylene terephtalate, pluronics, high-density polyethylene, polypropylene, polysulfones, polyphenylene oxides, polymethylmethacrylate, polyetheretherketone, polylactide, polyglycolide, poly(lactide-co-glycolide), poly(dioxanone), poly([epsilon]-caprolactone), poly(methyl vinyl ether/maleic anhydride), poly(hydroxylbutyrate), poly(hydroxylvalerate), tyrosine-based polycarbonate, polypropylene fumarate, ionic polymers, poly(allylamine hydrochloride), poly(diallyldimethylammonium chloride), as well as derivates, mixtures and combinations thereof.

Suitable natural or biotechnologically derived polymeric materials include polysaccharides, cross-linked carboxyl-containing polysaccharides, xanthan, dextrane, pectinate, glucomannan gel, glycosaminoglycane, hyaluronic acid, chondroitin sulphate, heparin, keratane sulphate, chitosan, alginate, cellulose, hydroxyethylcellulose, carboxy-methylcellulose, cellulose phosphates, polyamino acids, polylysine, collagens, acylate proteins, poly(hydroxylbutyrate), as well as derivates, mixtures and combinations thereof.

Preferably the polymeric material is stabilized by chemical crosslinking, ionic interactions, van-der-Waals interactions, embedding of foreign phase material, fibre reinforcement, or any combination thereof. Chemical crosslinking and fibre reinforcement being preferred.

The stabilization by chemical crosslinking is achieved with various approaches preferably including direct reaction between polymer molecules and/or reaction with functional crosslinking agents.

The chemical crosslinking reaction may be induced by various methods including chemical activation, light induction, e-beam irradiation, gamma irradiation, heat treatment and/or microwave treatment, or any combination thereof.

Suitable fibre reinforcement additives are preferably selected from the group consisting of metallic fibres, ceramic fibres, polymeric fibres, carbon fibres, KEVLAR® fibres, SPECTRA® fibres, polyester fibres, hydroxyapatite particles, short fibres, long fibres, continuous fibres, nano fibres, mono filaments, multi filaments, woven, knitted or spun bonded fibres or filaments, mesh and mixtures thereof.

In another preferred embodiment, the material of the implant device is impregnated with one or more pharmaceutical substances for influencing the surrounding tissue(s).

In a method for manufacturing an implant device according to the invention, the body preferably is formed by a polymer material. A stiffness gradient and/or the partial anisotropy in the polymeric material can be achieved through partly orienting the molten or semi-molten polymer material, through a layer-by-layer curing and/or crosslinking process, wherein the same chemical formulation is exposed to different crosslinking conditions, or wherein the chemical formulation is varied and exposed to the same or different crosslinking conditions. Further, a stiffness gradient and/or the partial anisotropy in the polymeric material can be achieved through introducing oriented or non-oriented fibre reinforcement additives into the polymer material. In a layer-by-layer curing and/or crosslinking process, the oriented or non-oriented fibre reinforcement may be introduced into part of the polymer material. The layer-by-layer build-up can be done for example in a centro symmetric way and/or in a contoured way, whereby the final shape of the device is closer to the shape of the natural structure it is to replace, e.g. natural meniscus or natural spinal disc.

The device according to the invention may be implanted using standard orthopaedic surgery techniques. For a meniscal implant for example, prior to use, it must be confirmed that the ligamentous structures in the knee are intact. This can be done using a variety of methods. One in particular that is non-invasive, is magnetic resonance imaging (MRI). Unlike other implant devices, after implantation, the joint area may be viewed using a Magnetic Resonance Imager (MRI) since the device according to the invention preferably does not contain metal parts which would cause interference. The device may more preferably also contain radio-opaque markers to better locate the device with X-ray images and/or an inorganic contrast agent for computer tomography (CT) imaging.

EXAMPLES

Example 1

An implant device according to claim 1 is made by co-polymerization of HEMA and MMA. The device is engineered in several steps with changing ratios of HEMA and MMA creating a transversal gradient in stiffness with minima and maxima. The water content of the polymer ranges between 10% and 20%. The compressive strength varies between 0.5 MPa and 5 MPa. The device is mechanically shaped to conform with the required dimensions.

Example 2

An implant device according to claim 1 is made by co-polymerization of HEMA and MMA. The device is engineered in several steps with changing ratios of HEMA and MMA and by addition a gradient of hyaluronic acid containing solvent. The water content of the polymer ranges between 15% and 30%. The stiffness varies between 0.5 MPa and 2 MPa. The device is mechanically shaped in dry state, rehydrated and resurfaced to conform the required dimensions.

Example 3

An implant device is made by co-polymerization of urethane derivatives, hydroxylbutyrate and a cellulose derivative. The device is polymerized in an one-step process by UV irradiation allowing for local control of the crosslink density. The Young's modulus is between 1 MPa and 80 MPa. The deformation under physiological load is less than 5%.

Example 4

An implant device is made by layer-by-layer polymerization of poly-vinyl-alcohol and silicone. A gradient in mechanical properties is achieved by slowly changing the polymerization conditions. The achieved stiffness is between 0.5 MPa and 5 MPa.

Example 5

An implant device is made by co-polymerization of a silicone and a biotechnologically derived chitosan. The gradient is created by selective UV irradiation. The Young's modulus varies between 1 MPa and 20 MPa with a transversal dimensional stability of >95%. The shape of the device is attained by polymerization in preforms.

Example 6

An implant device is made of polyurethanecarbonate. During polymerization 10% (w/w) of an inorganic contrast agent is added for CT imaging. The stiffness of the polymer is varied by controlling selectively the polymerization reaction. A Young's modulus of up to 200 MPa is achieved. The transversal dimensional stability was >99%.

The invention claimed is:

1. An inter-condylar implant device comprising a body having a stiffness gradient with at least one minimum along the x-axis and/or along the y-axis, wherein the body has a limited dimensional deformation, limited by material properties of the implant body, in the direction of the x-axis and/or y-axis under maximum physiological load condition, wherein the relative dimensional deformation is below 10% in the direction corresponding to the x- and/or y-axis, based on the dimension under no load condition compared to the dimension under a maximum load condition in the z-direction ranging from 20 MPa to 200 MPa, and wherein the stiffness of the implant body is at least partially anisotropic.

2. The implant device according to claim 1, wherein the stiffness gradient is continuous.

3. The implant device according to claim 1, wherein the stiffness gradient is discontinuous.

4. The implant device according to claim 1, wherein the body has a stiffness gradient with at least two minima along the x-axis and/or y-axis.

5. The implant device according to claim 1, wherein the device is an interspace implant, in particular an inter-condylar implant or a spinal disc implant.

6. The implant device according to claim 1, wherein the shape of the device conforms to the physiological situation upon implantation.

7. The implant device according to claim 1, wherein the device is self-centering in the physiological space it is implanted in.

8. The implant device according to claim 1, wherein the device has a stiffness corresponding to a Young modulus ranging from at least 0.1 to 100 MPa in each direction when the material is modeled as linear elastic.

9. The implant device according to claim 1, wherein the device has a dynamic coefficient of friction below 0.1.

10. The implant device according to claim 1, wherein the body is comprised of a polymer material.

11. The implant device according to claim 10, wherein the polymer material is a hydrogel.

12. The implant device according to claim 10, wherein the polymer material is biocompatible.

13. A method for manufacturing an inter-condylar implant device according to claim 1, wherein the body is formed by a polymer material, and wherein the stiffness gradient and/or the partial anisotropy is created (a) through partly orienting the molten or semi-molten polymer material, or (b) through a layer-by-layer curing and/or crosslinking process, or (c) through introducing oriented or non-oriented fibre reinforcement into part of the polymer material.

* * * * *